United States Patent
Quere

(10) Patent No.: US 8,211,936 B2
(45) Date of Patent: Jul. 3, 2012

(54) CO-CRYSTALS OF PYRROLIDINONES

(75) Inventor: Luc Quere, Sombreffe (BE)

(73) Assignee: UCB Pharma, S.A., Brussels (BE)

( * ) Notice: Subject to any disclaimer, the term of this patent is extended or adjusted under 35 U.S.C. 154(b) by 359 days.

(21) Appl. No.: 12/303,672

(22) PCT Filed: Jun. 6, 2007

(86) PCT No.: PCT/EP2007/005009
§ 371 (c)(1), (2), (4) Date: May 3, 2010

(87) PCT Pub. No.: WO2007/141002
PCT Pub. Date: Dec. 13, 2007

(65) Prior Publication Data
US 2010/0240728 A1  Sep. 23, 2010

(30) Foreign Application Priority Data
Jun. 8, 2006 (EP) .................................. 06011826

(51) Int. Cl.
*A01N 43/36* (2006.01)
*A61K 31/40* (2006.01)

(52) U.S. Cl. ....................... 514/424; 548/550

(58) Field of Classification Search .......... 514/424; 548/550
See application file for complete search history.

(56) References Cited

FOREIGN PATENT DOCUMENTS

| WO | 01/62726 A2 | 8/2001 |
| WO | WO 01/62726 | * 8/2001 |
| WO | WO 03/094913 | * 11/2003 |
| WO | 2004/078161 A | 9/2004 |
| WO | WO 2004/078161 | * 9/2004 |

OTHER PUBLICATIONS

Vishweshwar et al. (J. Pharm. Sciences 95 (3), Mar. 2006; p. 499-516.*

* cited by examiner

*Primary Examiner* — Andrew D Kosar
*Assistant Examiner* — Valerie Rodriguez-Garcia
(74) *Attorney, Agent, or Firm* — McDonnell Boehnen Hulbert & Berghoff LLP

(57) ABSTRACT

The present invention relates to new co-crystals of pyrrolidinones having the formula (I) wherein $R^1$ is a $C_1$-$C_6$ alkyl group. $R^2$ is a $C_1$-$C_6$ alkyl group which is optionally substituted by 1 to 3 halogens or $R^2$ is a $C_2$-$C_6$ alkenyl group.

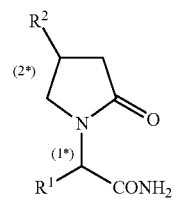

9 Claims, 1 Drawing Sheet

CO-CRYSTALS OF PYRROLIDINONES

This application is a US national phase of International Application No. PCT/EP2007/05009 filed on Jun. 6, 2007, the disclosure of which is incorporated herein by reference.

INTRODUCTION

Active pharmaceutical ingredients (API or APIs) in pharmaceutical compositions may be prepared in a variety of different forms. Such APIs can be prepared so as to have a variety of different chemical forms including chemical derivatives or salts. Such APIs can also be prepared to have different physical forms. APIs may for instance be amorphous, they may have different crystalline polymorphs, or may exist in different solvation or hydration states. By varying the form of an API, it is possible to vary the physical properties thereof. For example, crystalline polymorphs typically have e.g. different solubilities from one another, such that a more thermodynamically stable polymorph is less soluble than a less thermodynamically stable polymorph at a given temperature. Pharmaceutical polymorphs can also differ in properties such as shelf-life, bioavailability, morphology, vapour pressure, density, colour, viscosity, melting point and compressibility. Accordingly, variation of the crystalline state of an API is one of many ways in which to modulate the physical properties thereof.

Frequently there is a need for a new form of these APIs that have improved properties, in particular, in as far as oral formulations are concerned. Specifically, it may be desirable to identify improved forms of APIs that exhibit significantly improved properties including increased aqueous solubility, melting point of the solid form as well as the stability of the API. Furthermore, it is desirable to improve the processability, or preparation of pharmaceutical formulations. For example, needle-like crystal forms or habits of APIs can cause aggregation, even in compositions where the API is mixed with other substances, such that a non-uniform mixture is obtained. It may also be desirable to increase or decrease the dissolution rate of API-containing pharmaceutical compositions in water, increase and provide a more rapid or more delayed onset to therapeutic effect or control the bioavailability of orally-administered compositions in order to avoid any systemic absorption but only promoting local effect. It is also desirable to have a form of the API which, when administered to a subject, reaches a peak plasma level faster or slower, has a longer lasting therapeutic plasma concentration, and higher or lower overall exposure when compared to equivalent amounts of the API in its presently-known form.

Finally, it may be desired to provide for a form of the API having an increased melting point in such a way that it may be better formulated as an orally available product.

WO 01/62726 relates to pyrrolidinones, their synthesis as well as their medical use in the treatment of various CNS disorders like epilepsy. WO 01/62726 specifically describes the synthesis of the two diastereoisomers of 2-[4-(2,2-difluorovinyl)-2-oxopyrrolidinyl]-butanamide. It also describes the synthesis of the two diastereoisomers of (2S)-2-(2-oxo-4-n-propyl-1-pyrrolidinyl)butanamide.

SUMMARY OF THE INVENTION

The present invention relates to new co-crystals of pyrrolidinones having the formula (I)

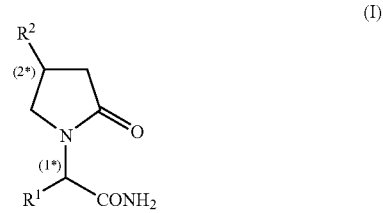

wherein
$R^1$ is a $C_1$-$C_6$ alkyl group (e.g. a methyl or an ethyl).
$R^2$ is a $C_1$-$C_6$ alkyl group (e.g. a methyl or ethyl or propyl) which may optionally be substituted by 1 to 3 halogens or $R^2$ is a $C_2$-$C_6$ alkenyl group which is optionally substituted by 1 to 3 halogens (e.g. a difluorovinyl) obtained by crystallisation with a salt selected from $MgCl_2$, $MgSO_4$, $MgBr_2$, $Mg_3(PO4)_2$, $MgHPO4$, $Mg(H_2PO_4)_2$, $MgCO_3$, $Mg(HCO_3)_2$, $CaCl_2$, $CaSO_4$, $CaBr_2$, $CaCO_3$, $Mg(HCO_3)_2$, $Ca_3(PO4)_2$, $CaHPO4$, $Ca(H_2PO_4)_2$, $KCl$, $KBr$, $K_2SO_4$, $KHSO_4$, $K_2CO_3$, $K_2HPO_4$, $KH_2PO_4$, $K_3PO_4$, $NaCl$, $NaBr$, $Na_2SO_4$, $Na_2CO_3$, $Na_2HPO_4$, $NaH_2PO_4$, $Na_3PO_4$, $NH_4Cl$, $NH_4Br$, $(NH_4)_2SO_4$, $(NH_4)_2CO_3$, $(NH_4)_2HPO_4$, $NH_4H_2PO_4$, $Na_3PO_4$ and their hydrates, as well as magnesium or calcium or potassium or sodium or ammonium salts of pharmaceutically accepted organic acids like malic acid, maleic acid, citric acid, pamoic acid, acetic acid, lactic acid, fumaric acid, methyl sulfonic acid, mesylic acid, ascorbic acid and the like, either individually or in combination.

The invention also comprises a pharmaceutical composition containing new co-crystals of pyrrolidinones having the formula (I) as well as a method for preparing such formulation and the use of said formulation for the treatment of epilepsy, epileptogenesis, seizure disorders, convulsions and other neurological disorders including bipolar disorders, mania, depression, anxiety, migraine, trigeminal and other neuralgia, chronic pain, neuropathic pain, cerebral ischemia, cardiac arrhythmia, myotonia, cocaine abuse, stroke, myoclonus, essential tremor and other movement disorders, neonatal cerebral haemorrhage, amyotrophic lateral sclerosis, spasticity, Parkinson's disease and other degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

The molecule has at positions (1*) and (2*) an asymmetric carbon atom. All diastereomers are covered by formula (I).

The API co-crystals of the present invention have a significantly higher melting point than the APIs described in WO 01/62726.

DETAILED DESCRIPTION OF THE INVENTION

Figure 1:
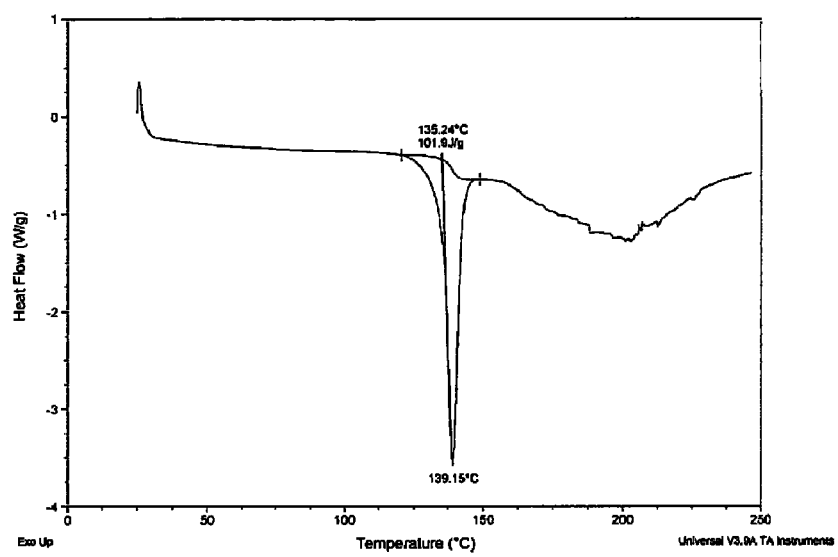
FIG. 1 relates to a DSC thermogram of a (2S)-2-[(4S)-4-(2,2-difluorovinyl)-2-oxopyrrolidinyl]-butanamide:$MgCl_2$:$H_2O$ (2:1:4) co-crystal.

In a specific embodiment the present invention relates to new co-crystals of pyrrolidinones having the formula (I)

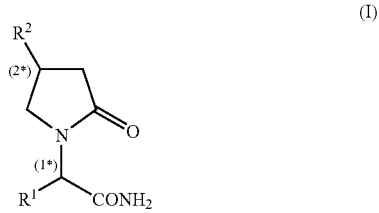

wherein
$R^1$ is a $C_1$-$C_6$ alkyl group (e.g. a methyl or an ethyl).
$R^2$ is a $C_1$-$C_6$ alkyl group (e.g. a methyl or ethyl or propyl) which may optionally be substituted by 1 to 3 halogens or $R^2$ is a $C_2$-$C_6$ alkenyl group which is optionally substituted by 1 to 3 halogens (e.g. a difluorovinyl) obtained by crystallisation with a salt selected from $MgCl_2$, $MgSO_4$, $MgBr_2$, $Mg_3(PO4)_2$, $MgHPO4$, $Mg(H_2PO_4)_2$, $MgCO_3$, $Mg(HCO_3)_2$, $Mg(HCO_3)_2$. $MgCl_2$, $MgSO_4$, $MgBr_2$ are particularly preferred.

In one embodiment the present invention relates to the specific API which is 2-[4-(2,2-difluorovinyl)-2-oxopyrrolidinyl]butanamide.

Accordingly, in a first aspect, the present invention provides a co-crystal of 2-[4-(2,2-difluorovinyl)-2-oxopyrrolidinyl]butanamide and either of $MgCl_2$, $MgSO_4$, $MgBr_2$, $Mg_3(PO4)_2$, $MgHPO4$, $Mg(H_2PO_4)_2$, $MgCO_3$, $Mg(HCO_3)_2$, $CaCl_2$, $CaSO_4$, $CaBr_2$, $CaCO_3$, $Mg(HCO_3)_2$, $Ca_3(PO4)_2$, $CaHPO4$, $Ca(H_2PO_4)_2$, KCl, KBr, $K_2SO_4$, $KHSO_4$, $K_2CO_3$, $K_2HPO_4$, $KH_2PO_4$, $K_3PO_4$, NaCl, NaBr, $Na_2SO_4$, $Na_2CO_3$, $Na_2HPO_4$, $NaH_2PO_4$, $Na_3PO_4$, $NH_4Cl$, $NH_4Br$, $(NH_4)_2SO_4$, $(NH_4)_2CO_3$, $(NH_4)_2HPO_4$, $NH_4H_2PO_4$, $Na_3PO_4$ and their hydrates, as well as magnesium or calcium or potassium or sodium or ammonium salts of pharmaceutically accepted organic acids like malic acid, maleic acid, citric acid, pamoic acid, acetic acid, lactic acid, fumaric acid, methyl sulfonic acid, mesylic acid, ascorbic acid and the like, either individually or in combination.

A second aspect of the present invention consists in a pharmaceutical composition comprising the co-crystal of 2-[4-(2,2-difluorovinyl)-2-oxopyrrolidinyl]butanamide and $MgCl_2$, $MgSO_4$, $MgBr_2$, $Mg_3(PO4)_2$, $MgHPO4$, $Mg(H_2PO_4)_2$, $MgCO_3$, $Mg(HCO_3)_2$, $CaCl_2$, $CaSO_4$, $CaBr_2$, $CaCO_3$, $Mg(HCO_3)_2$, $Ca_3(PO4)_2$, $CaHPO4$, $Ca(H_2PO_4)_2$, KCl, KBr, $K_2SO_4$, $KHSO_4$, $K_2CO_3$, $K_2HPO_4$, $KH_2PO_4$, $K_3PO_4$, NaCl, NaBr, $Na_2SO_4$, $Na_2CO_3$, $Na_2HPO_4$, $NaH_2PO_4$, $Na_3PO_4$, $NH_4Cl$, $NH_4Br$, $(NH_4)_2SO_4$, $(NH_4)_2CO_3$, $(NH_4)_2HPO_4$, $NH_4H_2PO_4$, $Na_3PO_4$ and their hydrates, as well as magnesium or calcium or potassium or sodium or ammonium salts of pharmaceutically accepted organic acids like malic acid, maleic acid, citric acid, pamoic acid, acetic acid, lactic acid, fumaric acid, methyl sulfonic acid, mesylic acid, ascorbic acid and the like, either individually or in combination.

Another aspect of the present invention provides a process for the preparation of a pharmaceutical composition, which process comprises the step of providing a co-crystal of 2-[4-(2,2-difluorovinyl)-2-oxopyrrolidinyl]butanamide and either of $MgCl_2$, $MgSO_4$, $MgBr_2$, $Mg_3(PO4)_2$, $MgHPO4$, $Mg(H_2PO_4)_2$, $MgCO_3$, $Mg(HCO_3)_2$, $CaCl_2$, $CaSO_4$, $CaBr_2$, $CaCO_3$, $Mg(HCO_3)_2$, $Ca_3(PO4)_2$, $CaHPO4$, $Ca(H_2PO_4)_2$, KCl, KBr, $K_2SO_4$, $KHSO_4$, $K_2CO_3$, $K_2HPO_4$, $KH_2PO_4$, $K_3PO_4$, NaCl, NaBr, $Na_2SO_4$, $Na_2CO_3$, $Na_2HPO_4$, $NaH_2PO_4$, $Na_3PO_4$, $NH_4Cl$, $NH_4Br$, $(NH_4)_2SO_4$, $(NH_4)_2CO_3$, $(NH_4)_2HPO_4$, $NH_4H_2PO_4$, $Na_3PO_4$ and their hydrates, as well as magnesium or calcium or potassium or sodium or ammonium salts of pharmaceutically accepted organic acids like malic acid, maleic acid, citric acid, pamoic acid, acetic acid, lactic acid, fumaric acid, methyl sulfonic acid, mesylic acid, ascorbic acid and the like, either individually or in combination.

In a preferred embodiment the API is the specific diastereomer being in clinical development having the INN seletracetam, i.e. (2S)-2-[(4S)-4-(2,2-difluorovinyl)-2-oxo-pyrrolidinyl]butanamide.

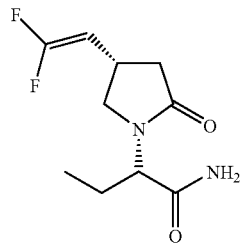

In a further embodiment the present invention relates to the specific API which is (2S)-2-(2-oxo-4-n-propyl-1-pyrrolidinyl)butanamide.

Accordingly, in a fourth aspect, the present invention provides a co-crystal of (2S)-2-(2-oxo-4-n-propyl-1-pyrrolidinyl)butanamide and either of $MgCl_2$, $MgSO_4$, $MgBr_2$, $Mg_3(PO4)_2$, $MgHPO4$, $Mg(H_2PO_4)_2$, $MgCO_3$, $Mg(HCO_3)_2$, $CaCl_2$, $CaSO_4$, $CaBr_2$, $CaCO_3$, $Mg(HCO_3)_2$, $Ca_3(PO4)_2$, $CaHPO4$, $Ca(H_2PO_4)_2$, KCl, KBr, $K_2SO_4$, $KHSO_4$, $K_2CO_3$, $K_2HPO_4$, $KH_2PO_4$, $K_3PO_4$, NaCl, NaBr, $Na_2SO_4$, $Na_2CO_3$, $Na_2HPO_4$, $NaH_2PO_4$, $Na_3PO_4$, $NH_4Cl$, $NH_4Br$, $(NH_4)_2SO_4$, $(NH_4)_2CO_3$, $(NH_4)_2HPO_4$, $NH_4H_2PO_4$, $Na_3PO_4$ and their hydrates, as well as magnesium or calcium or potassium or sodium or ammonium salts of pharmaceutically accepted organic acids like malic acid, maleic acid, citric acid, pamoic acid, acetic acid, lactic acid, fumaric acid, methyl sulfonic acid, mesylic acid, ascorbic acid and the like, either individually or in combination.

A fifth aspect of the present invention consists in a pharmaceutical composition comprising the co-crystal of (2S)-2-(2-oxo-4-n-propyl-1-pyrrolidinyl)butanamide and either of $MgCl_2$, $MgSO_4$, $MgBr_2$, $Mg_3(PO4)_2$, $MgHPO4$, $Mg(H_2PO_4)_2$, $MgCO_3$, $Mg(HCO_3)_2$, $CaCl_2$, $CaSO_4$, $CaBr_2$, $CaCO_3$, $Mg(HCO_3)_2$, $Ca_3(PO4)_2$, $CaHPO4$, $Ca(H_2PO_4)_2$, KCl, KBr, $K_2SO_4$, $KHSO_4$, $K_2CO_3$, $K_2HPO_4$, $KH_2PO_4$, $K_3PO_4$, NaCl, NaBr, $Na_2SO_4$, $Na_2CO_3$, $Na_2HPO_4$, $NaH_2PO_4$, $Na_3PO_4$, $NH_4Cl$, $NH_4Br$, $(NH_4)_2SO_4$, $(NH_4)_2CO_3$, $(NH_4)_2HPO_4$, $NH_4H_2PO_4$, $Na_3PO_4$ and their hydrates, as well as magnesium or calcium or potassium or sodium or ammonium salts of pharmaceutically accepted organic acids like malic acid, maleic acid, citric acid, pamoic acid, acetic acid, lactic acid, fumaric acid, methyl sulfonic acid, mesylic acid, ascorbic acid and the like, either individually or in combination.

A sixth aspect of the present invention consists in a process for the preparation of a pharmaceutical composition, which process comprises the step of providing a co-crystal of 2-[4-(2,2-difluorovinyl)-2-oxopyrrolidinyl]butanamide and either of $MgCl_2$, $MgSO_4$, $MgBr_2$, $Mg_3(PO4)_2$, $MgHPO4$, $Mg(H_2PO_4)_2$, $MgCO_3$, $Mg(HCO_3)_2$, $CaCl_2$, $CaSO_4$, $CaBr_2$, CaCO₃, Mg(HCO₃)₂, Ca₃ (PO4)₂, CaHPO4, Ca(H₂PO₄)₂, KCl, KBr, K₂SO₄, KHSO₄, K₂CO₃, K₂HPO₄, KH₂PO₄, K₃PO₄, NaCl, NaBr, Na₂SO₄, Na₂CO₃, Na₂HPO₄, NaH₂PO₄, Na₃PO₄, NH₄Cl, NH₄Br, (NH₄)₂SO₄, (NH₄)₂CO₃, (NH₄)₂HPO₄, NH₄H₂PO₄, Na₃PO₄ and their hydrates, as well as magnesium or calcium or potassium or sodium or ammonium salts of pharmaceutically accepted organic acids like malic acid, maleic acid, citric acid, pamoic acid, acetic acid, lactic acid, fumaric acid, methyl sulfonic acid, mesylic acid, ascorbic acid and the like, either individually or in combination.

In a specific embodiment the API is the diastereomer being in clinical development having the INN brivaracetam, i.e. ((2S)-2-((4R)-2-oxo-4-n-propyl-1-pyrrolidinyl)butanamide.

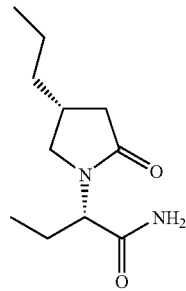

In still a further embodiment, the co-crystal is a hydrate of the API according to formula (I) and either of MgCl₂, MgSO₄, MgBr₂, Mg₃ (PO4)₂, MgHPO4, Mg(H₂PO₄)₂, MgCO₃, Mg(HCO₃)₂, CaCl₂, CaSO₄, CaBr₂, CaCO₃, Mg(HCO₃)₂, Ca₃ (PO4)₂, CaHPO4, Ca(H₂PO₄)₂, KCl, KBr, K₂SO₄, KHSO₄, K₂CO₃, K₂HPO₄, KH₂PO₄, K₃PO₄, NaCl, NaBr, Na₂SO₄, Na₂CO₃, Na₂HPO₄, NaH₂PO₄, Na₃PO₄, NH₄Cl, NH₄Br, (NH₄)₂SO₄, (NH₄)₂CO₃, (NH₄)₂HPO₄, NH₄H₂PO₄, Na₃PO₄ and their hydrates, as well as magnesium or calcium or potassium or sodium or ammonium salts of pharmaceutically accepted organic acids like malic acid, maleic acid, citric acid, pamoic acid, acetic acid, lactic acid, fumaric acid, methyl sulfonic acid, mesylic acid, ascorbic acid and the like, either individually or in combination.

For the specific API (2S)-2-[(4S)-4-(2,2-difluorovinyl)-2-oxopyrrolidinyl]butanamide the stoechiometry of the co-crystal with MgCl₂ may be as follows:
(2S)-2-[(4S)-4-(2,2-difluorovinyl)-2-oxopyrrolidinyl]butanamide×0.5 MgCl₂×2H₂O For the specific API ((2S)-2-((4R)-2-oxo-4-n-propyl-1-pyrrolidinyl) butanamide the stoechiometry of the co-crystal with MgCl₂ may be as follows:
(2S)-2-((4R)-2-oxo-4-n-propyl-1-pyrrolidinyl) butanamide× 0.5 MgCl₂×2H₂O The API co-crystals have a significantly higher melting point than the APIs alone. This has a major advantage when formulating the API to provide a pharmaceutical composition. It is not desirable to formulate an API which has a low melting point. Generally, the low melting point of the uncomplexed API renders it more difficult to manufacture tablets thereof. Tablets are the most favored of orally deliverable drug formulations.

The melting point of (2S)-2-[(4S)-4-(2,2-difluorovinyl)-2-oxopyrrolidinyl]butanamide is thereby increased from 77° C. to about 139° C. for the co-crystal with MgCl₂.

The melting point of ((2S)-2-((4R)-2-oxo-4-n-propyl-1-pyrrolidinyl)butanamide is thereby increased from 78° C. to about 134° C. for the co-crystal with MgCl₂.

A further aspect of the present invention consists in a method for preparing pyrrolidinone co-crystals, said method comprising the step of crystallizing the pyrrolidinone according to formula (I) in a solvent which comprises and either of MgCl₂, MgSO₄, MgBr₂, Mg₃ (PO4)₂, MgHPO4, Mg(H₂PO₄)₂, MgCO₃, Mg(HCO₃)₂, CaCl₂, CaSO₄, CaBr₂, CaCO₃, Mg(HCO₃)₂, Ca₃ (PO4)₂, CaHPO4, Ca(H₂PO₄)₂, KCl, KBr, K₂SO₄, KHSO₄, K₂CO₃, K₂HPO₄, KH₂PO₄, K₃PO₄, NaCl, NaBr, Na₂SO₄, Na₂CO₃, Na₂HPO₄, NaH₂PO₄, Na₃PO₄, NH₄Cl, NH₄Br, (NH₄)₂SO₄, (NH₄)₂CO₃, (NH₄)₂HPO₄, NH₄H₂PO₄, Na₃PO₄ and their hydrates, as well as magnesium or calcium or potassium or sodium or ammonium salts of pharmaceutically accepted organic acids like malic acid, maleic acid, citric acid, pamoic acid, acetic acid, lactic acid, fumaric acid, methyl sulfonic acid, mesylic acid, ascorbic acid and the like, either individually or in combination.

A still further aspect of the present invention consists in a method for purifying the pyrrolidinone according to formula (I) by the use of a co-crystallization process.

A preferred solvent for obtaining the co-crystals is water, more preferred is an alcoholic solvent, e.g. an aqueous mixture containing methanol, or methanol alone, toluene, ethyl acetate or isopropyl acetate.

The pharmaceutical compositions according to the present invention are useful for treating epilepsy, epileptogenesis, seizure disorders, convulsions and other neurological disorders including bipolar disorders, mania, depression, anxiety, migraine, trigeminal and other neuralgia, chronic pain, neuropathic pain, cerebral ischemia, cardiac arrhythmia, myotonia, cocaine abuse, stroke, myoclonus, essential tremor and other movement disorders, neonatal cerebral haemorrhage, amyotrophic lateral sclerosis, spasticity, Parkinson's disease and other degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

Pharmaceutical compositions of the invention may optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a co-crystal of the present invention once the salt has been dissolved in a solution. Suitable binding agents and adhesives include, but are not limited to, either individually or in combination, acacia gum; tragacanth gum; sucrose; gelatin; glucose; starches such as, but not limited to pregelatinized starches (e.g. National TM 1511 and National Tm1500); celluloses such as, but not limited to, methylcellulose (e.g. Tylose™) and carmellose sodium, alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g. Klucel™ of Aqualon™); and ethylcellulose (e.g. Ethocel™ of the Dow Chemical Company).

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these unit ratios in a given polymer affects properties and performance. Examples of block co-polymers with varying compositions of block units are Poloxamer 188 and Poloxamer 237 (BASF Corporation).

Pharmaceutical compositions of the invention optionally comprise one or more pharmaceutically acceptable wetting agents as excipients. Such wetting agents are preferably selected to maintain the co-crystal in close association with water, a condition that is believed to improve bioavailability of the composition. Such wetting agents can also be useful in solubilizing or increasing the solubility of co-crystals.

Non-limiting examples of surfactants that can be used as wetting agents in pharmaceutical compositions of the invention include quaternary ammonium compounds, for example benzalkonium chloride, benzethonium chloride and cetylpyridinium chloride, dioctylsodium sulfosuccinate, polyoxyethylene alkylphenyl ethers, for example nonoxynol 9, nonoxynol 10, and degrees Ctoxynol 9, poloxamers (polyoxyethylene and polyoxypropylene blockcopolymers 9 polyoxyethylene fatty acid glycerides and oils, for example polyoxyethylene(8)caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween 80™ of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof.

Wetting agents that are anionic surfactants are preferred. Sodium lauryl sulfate is a particularly preferred wetting agent Pharmaceutical compositions of the invention optionally comprise one or more pharmaceutically acceptable lubricants (including anti-adherents and/or glidants) as excipients. Suitable lubricants include, but are not limited to, either individually or in combination, glycerylbehapate (e.g., Compritol™ 888 of Gattefosse); stearic acid and salts thereof, including magnesium, calcium and sodium stearate; hydrogenated vegetable oils (e.g. Sterotexof Abitec); colloidal silica; talc; waxes; boric acid; sodium benzoate; sodium acetate; sodium fumarate; sodium chloride; DL-leucine; PEG (e.g. Carbowax 4000 and Carbowax 6000 of the Dow Chemical Company); sodium oleate; sodium lauryl sulfate; and magnesium lauryl sulfate Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearate. Talc is a preferred anti-adherent or glidant used, for example, to reduce formulation sticking to equipment surfaces and also to reduce static in the blend. Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in pharmaceutical compositions of the present invention. Tablets can be coated, for example with an enteric coating, or uncoated.

Compositions of the invention can further comprise, for example, buffering agents.

Optionally, one or more effervescent agents can be used as disintegrants and/or to enhance organoleptic properties of pharmaceutical compositions of the invention According to an embodiment of the invention, an effervescent agent, present in a solid dosage form in an amount less than that effective to promote disintegration of the dosage form, provides improved dispersion of the API in an aqueous medium.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g. calcium carbonate), bicarbonate salts (e.g. sodium bicarbonate), sesquicarbonate salts, and mixtures thereof. Non-limiting examples of suitable acids as components of effervescent agents and/or solid organic acids useful in the invention include citric acid, tartaric acid (as D-, L-, or D/L-tartaric acid), malic acid (as D-, L-, or DL-malic acid), maleic acid, fumaric acid, adipic acid, succinic acid, acid anhydrides of such acids, acid salts of such acids, and mixtures thereof. Citric acid is a preferred acid.

Excipients which solubilize APIs typically have both hydrophilic and hydrophobic regions, or are preferably amphiphilic or have amphiphilic regions. One type of amphiphilic or partially-amphiphilic excipient comprises an amphiphilic polymer. A specific amphiphilic polymer is a polyalkylene glycol, which is commonly comprised ethylene glycol and/or propylene glycol subunits. Such polyalkylene glycols can be esterified at their termini by a carboxylic acid, ester, acid anhyride or other suitable moiety. Examples of such excipients include poloxamers (symmetric block copolymers of ethylene glycol and propylene glycol; e.g., poloxamer 237), polyalkyene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a polyalkylene glycol to produce a mixture of mono-, di- and tri-glycerides and mono- and di-esters; e.g., stearoyl macrogol-32 glycerides). Such pharmaceutical compositions are advantageously administered orally.

Solid dosage forms of the invention can be prepared by any suitable process, not limited to processes described herein.

An illustrative process comprises (a) a step of blending an API of the invention with one or more excipients to form a blend, and (b) a step of tableting or encapsulating the blend to form tablets or capsules, respectively.

In a preferred process, solid dosage forms are prepared by a process comprising (a) a step of blending a co-crystal of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a dry granulation step. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in API content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein an API is suspended with one or more excipients in one or more sprayable liquids, preferably a non-protic (e.g., non-aqueous or non-alcoholic) sprayable liquid, and then is rapidly spray dried over a current of warm air.

A granulate or spray dried powder resulting from any of the above illustrative processes can be compressed or molded to prepare tablets or encapsulated to prepare capsules.

Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Pharmaceutically acceptable co-crystals can be administered by controlled-, sustained-, or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Chemgju, Controlled Ilelease Dosage Form Design, Technomic Publishing, Lancaster, Pa.: 2000).

EXPERIMENTAL PART

Example 1

Preparation of a co-crystal of (2S)-2-[(4S)-4-(2,2-difluorovinyl)-2-oxopyrrolidinyl]butanamide with $MgCl_2$ 151 mg (0.65 mmol) of (2S)-2-[(4S)-4-(2,2-difluorovinyl)-2-oxopyrrolidinyl]butanamide and 31 mg (0.325 mmol) of $MgCl_2$ are dissolved in approximately 3 mL of methanol. Slow evaporation of the solvent yields prismatic and colorless tablets of (2S)-2-[(4S)-4-(2,2-difluorovinyl)-2-oxopyrrolidinyl]butanamide:$MgCl_2$:$H_2O$ (2:1:4) co-crystal. The co-crystal may be analysed via DSC and single-crystal x-ray diffraction.

A thermal analysis (Q-1000, TA instrument) is performed to determine the melting point/behaviour of the (2S)-2-[(4S)-4-(2,2-difluorovinyl)-2-oxopyrrolidinyl]-butanamide: $MgCl_2$:$H_2O$ (2:1:4) co-crystal. The melting point is determined to be between 138-145 degrees C.

Single crystal x-ray data (NONIUS CAD-4/MACH$_3$): C20 H36 Cl2 F4 Mg N4 O8, M=631.74, trigonal P 32 21, a=8.850(2) angstroms, b=8.850(2) angstroms, c=34.827 (5) angstroms, alpha=90 degrees, beta=90 degrees, gamma=120 degrees, V=2362.3(8) cubic angstroms, T=293(2) K, Z=3, $D_C$=1.332 g/cm$^3$, $\lambda$=1.54178 angstroms. Final residuals for 194 parameters were $R_1\{I>2sigma(I)\}$=0.0498 and $wR_2$=0.147.

The (2S)-2-[(4S)-4-(2,2-difluorovinyl)-2-oxopyrrolidinyl]butanamide:$MgCl_2$:$H_2O$ (2:1:4) co-crystal lattice consists of lipophilic multilayers made up of the ethyl and the difluorovinyl chains. Attractive Van der Waals forces between those layers help to stabilize the molecular building, as well as a strong H-bonding network in the polar layers, formed by the polymeric strands of coordination spheres of magnesium cations.

The simulated x-ray powder pattern associated with this structure is characterized by the following peaks: 7.60, 11.54, 11.82, 12.60, 13.84, 15.38, 17.18, 19.16, 20.06, 20.20, 21.28, 23.48, 23.80, 26.52, 28.74, 30.54, 30.66, 31.28, 35.84, and 40.46 degrees 2-theta (data as simulated by Mercury 1.4.1)

Alternative approach to prepare (2S)-2-[(4S)-4-(2,2-difluorovinyl)-2-oxo-pyrrolidinyl]butanamide:$MgCl_2$: $H_2O$ (2:1:4) co-crystal: 4.96 g of (2S)-2-[(4S)-4-(2,2-difluorovinyl)-2-oxopyrrolidinyl]butanamide (0.0214 mol) is dissolved in 15 mL of MeOH. To this solution, 1.01 g of $MgCl_2$ (0.011 mol) is added. The solution is kept few days at room temperature. 20 mL of t-butyl-methyl ether is added. The solution turns white and visquous and a solid can be filtered. This yields in 5.90 g of white powder after one night at 30° C. under vacuum.

The powder may be characterized using DSC, XRPD, IR:

DSC thermogram (Q-1000, TA instrument) shows an endothermic transition corresponding to the melting of the co-crystal at about 139 degrees C. (peak, onset is 135 degrees C.), (See FIG. 1). This represents an increase of about 62° C. of the melting point compared to the known crystalline form of (2S)-2-[(4S)-4-(2,2-difluorovinyl)-2-oxo-pyrrolidinyl]butanamide.

Experimental x-ray powder data (PW3710 Philips Analytical X-Ray B.V., $\lambda$=1.54178 angstroms): The (2S)-2-[(4S)-4-(2,2-difluorovinyl)-2-oxopyrrolidinyl]-butanamide:$MgCl_2$:$H_2O$ (2:1:4) co-crystal can be characterized by any one, any two, any three, any four or more of the peaks including, but not limited to: 7.61, 11.57, 12.60, 13.85, 15.41, 17.21, 19.21, 20.25, 21.30, 23.81, 26.57, 30.69, 30.66, 35.93, and 40.49 degrees 2-theta (data as collected).

IR spectroscopy (Perkin Elmer System 2000 FTIR) shows absorptions at: 3307, 3193, 2974, 2943, 1756, 1659, 1625, 1420, 1310, 1269 and 926 cm$^1$.

Example 2

Preparation of a co-crystal of ((2S)-2-((4R)-2-oxo-4-n-propyl-1-pyrrolidinyl) butanamide with $MgCl_2$ To 300 μL of Water containing 36 mg (0.12 mmol) of ((2S)-2-((4R)-2-oxo-4-n-propyl-1-pyrrolidinyl)butanamide is added 31 mg (0.33 mmol) of $MgCl_2$. Slow evaporation of the solvent yields prismatic and colorless crystals of ((2S)-2-((4R)-2-oxo-4-n-propyl-1-pyrrolidinyl)butanamide:MgCl$_2$:H$_2$O (2:1:4) co-crystal. The co-crystal may be analysed via DSC and single-crystal x-ray diffraction.

A thermal analysis (Q-1000, TA instrument) is performed to determine the melting point/behaviour of the of ((2S)-2-((4R)-2-oxo-4-n-propyl-1-pyrrolidinyl) butan-amide:MgCl$_2$:H$_2$O (2:1:4) co-crystal. The melting point is determined to be at about 135 degrees C.

Single crystal x-ray data (NONIUS CAD-4/MACH3): C22 H48 Cl2 Mg N4 O8, M=591.85, monoclinic P 21, a=8.863(1) angstroms, b=23.742(2) angstroms, c=8.907 (1) angstroms, alpha=90 degrees, beta=116.86(1) degrees, gamma=90 degrees, V=1672.1(3) cubic angstroms, T=293(2) K, Z=2, D$_C$=1.176 g/cm$^3$, λ=1.54178 angstroms. Final residuals for 338 parameters are R$_1$\{I>2sigma(I)\}=0.0528 and wR$_2$=0.150.

The ((2S)-2-((4R)-2-oxo-4-n-propyl-1-pyrrolidinyl) butanamide:MgCl$_2$:H$_2$O (2:1:4) co-crystal crystal lattice consists of lipophilic multilayers made up of the ethyl and the propyl chains. Attractive Van der Waals forces between those layers help to stabilize the molecular building, as well as a strong H-bonding network in the polar layers, formed by the polymeric strands of coordination spheres of magnesium cations.

The simulated x-ray powder pattern associated with this structure is characterized by the following peaks: 7.44, 11.74, 12.26, 13.40, 14.92, 15.82, 18.64, 21.40, 21.80, 22.14, 22.68, 23.60, 23.70, 25.12, 26.80 degrees 2-theta (data as simulated by Mercury 1.4.1).

Alternative approach to prepare ((2S)-2-((4R)-2-oxo-4-n-propyl-1-pyrrolidinyl) butanamide:MgCl$_2$:H$_2$O (2:1:4) co-crystal: 4.96 g of (2S)-2-[(4S)-4-(2,2-difluorovinyl)-2-oxopyrrolidinyl]butanamide (0.023 mol) is dissolved in 5 mL of MeOH. To this solution, 1.01 g of MgCl$_2$ (0.010 mol) is added. The solution is kept 30 minutes at room temperature. 20 mL of ter-butyl-methyl ether is added. The solution becomes white and visquous. After evaporation of the solvents, the solid is washed with hexane and let to crystallize. This yields in 5 g of white powder after one night at 30° C. under vacuum.

Figure 2:
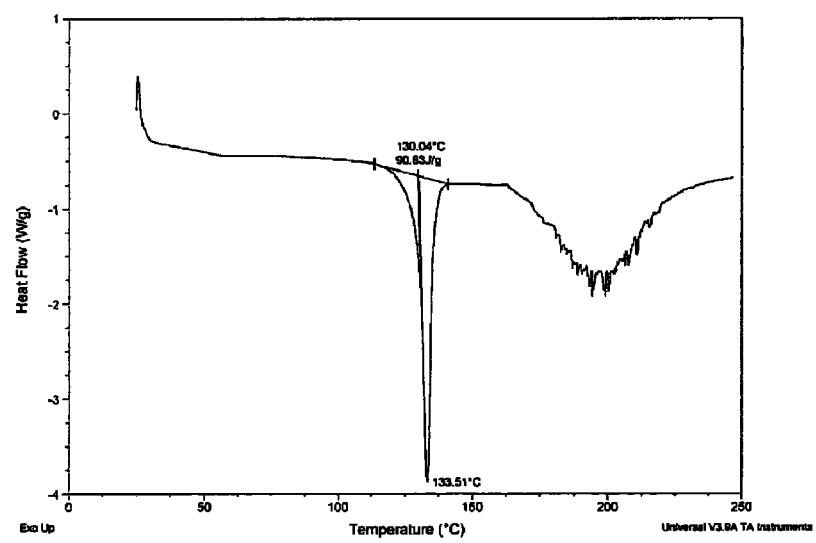
FIG. 2 relates to a DSC thermogram of a ((2S)-2-((4R)-2-oxo-4-n-propyl-1-pyrrolidinyl)butanamide:$MgCl_2$:$H_2O$ (2:1:4) co-crystal.

The crystals may be characterized using DSC, XRPD, IR.
DSC thermogram (Q-1000, TA instrument) shows an endothermic transition corresponding to the melting of the co-crystal at about 133.5 degrees C. (peak, onset is 130 degrees C.), (See FIG. 2). This represents an increase of 56° C. of the melting point compared to the known crystalline form of (2S)-2-((4R)-2-oxo-4-n-propyl-1-pyrrolidinyl)butanamide.

Experimental x-ray powder data (PW3710 Philips Analytical X-Ray B.V., λ=1.54178 angstroms): The x-ray pattern of ((2S)-2-((4R)-2-oxo-4-n-propyl-1-pyrrolidinyl) butan-amide:MgCl$_2$:H$_2$O (2:1:4) co-crystal can be characterized by any one, any two, any three, any four or more of the peaks including, but not limited to: 7.57, 11.21, 11.77, 12.29, 13.45, 15.05, 15.93, 18.77, 21.45, 22.21, 22.89, 25.21 and 26.89 degrees 2-theta (data as collected).

IR spectroscopy (Perkin Elmer System 2000 FTIR) shows absorptions at: 3311, 3180, 2966, 2936, 2875, 1654, 1494, 1458, 1420, 1291, 1273, 1206 and 938 cm$^{-1}$.

The invention claimed is:

1. A co-crystal comprising a pyrrolidinone compound which is (2S)-2-[(4S)-4-(2,2-difluorovinyl)-2-oxopyrrolidinyl]butanamide×0.5 MgCl$_2$×2H$_2$O.

2. The co-crystal according to claim 1 wherein the co-crystal has an X-ray powder diffraction (XRPD) pattern comprising any one, any two, any three, or any four or more of the XRPD peaks selected from the group consisting of 7.61, 11.57, 12.60, 13.85, 15.41, 17.21, 19.21, 20.25, 21.30, 23.81, 26.57, 30.69, 30.66, 35.93 and 40.49 degrees 2-theta.

3. A co-crystal comprising a pyrrolidinone which is ((2S)-2-((4R)-2-oxo-4-n-propyl-1-pyrrolidinyl)butanamide×0.5 MgCl$_2$×2H$_2$O.

4. The co-crystal according to claim 3, wherein the co-crystal has an x-ray powder diffraction pattern comprising XRPD peaks at 7.44, 11.74, 12.26, 13.40, 14.92, 15.82, 18.64, 21.40, 21.80, 22.14, 22.68, 23.60, 23.70, 25.12 and 26.80 degrees 2-theta.

5. A pharmaceutical composition which comprises a co-crystal according to claim 1, 2, 3, or 4 as well as a pharmaceutically acceptable excipient.

6. A method for treating epilepsy, epileptogenesis, and convulsions comprising administering an effective amount of a co-crystal according to claim 1, 2, 3, or 4.

7. A process for the preparation of a co-crystal according to claim 1, 2, 3, or 4 comprising crystallizing the pyrrolidinone compound in crude form from a solvent or a solvent mixture containing MgCl$_2$.

8. The process according to claim 7, wherein the solvent is water, or an alcohol, or an aqueous mixture containing an alcohol, or the solvent is toluene, ethyl acetate or isopropyl acetate as well as mixtures thereof.

9. The process according to claim 8, wherein the solvent is methanol.

* * * * *